United States Patent
Ishihara (10) Patent No.: US 9,168,024 B2
(45) Date of Patent: Oct. 27, 2015

(54) ULTRASOUND DIAGNOSTIC APPARATUS AND METHOD OF PRODUCING ULTRASOUND IMAGE

(75) Inventor: Keitarou Ishihara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 32 days.

(21) Appl. No.: 13/598,713

(22) Filed: Aug. 30, 2012

(65) Prior Publication Data
US 2013/0060142 A1    Mar. 7, 2013

(30) Foreign Application Priority Data

Sep. 7, 2011    (JP) .................................. 2011-194721

(51) Int. Cl.
| | |
|---|---|
| A61B 8/14 | (2006.01) |
| G01S 7/52 | (2006.01) |
| A61B 8/00 | (2006.01) |
| G01S 15/89 | (2006.01) |
| G10K 11/34 | (2006.01) |

(52) U.S. Cl.
CPC ................. *A61B 8/14* (2013.01); *A61B 8/4483* (2013.01); *A61B 8/4494* (2013.01); *G01S 7/52019* (2013.01); *G01S 15/8915* (2013.01); *G10K 11/346* (2013.01)

(58) Field of Classification Search
CPC ...... A61B 8/14; A61B 8/4494; A61B 8/4483; G01S 7/52019; G01S 15/8915; G01K 11/346
See application file for complete search history.

(56) References Cited

U.S. PATENT DOCUMENTS

| | | | | |
|---|---|---|---|---|
| 5,379,642 A | * | 1/1995 | Reckwerdt et al. | ............. 73/625 |
| 6,063,030 A | * | 5/2000 | Vara et al. | ..................... 600/437 |

FOREIGN PATENT DOCUMENTS

JP    2009-22656 A    2/2009

OTHER PUBLICATIONS

Lu et al., "Biomedical Ultrasound Beam Forming". Ultrasound in Med. & Biol. vol. 20, No. 5. 1994. pp. 403-428.*
Wikipedia "Data validation" edited Jul. 20, 2011, retrieved Sep. 16, 2014 from <http://en.wikipedia.org/w/index.php?title=Data_validation&oldid=440495763>.*

* cited by examiner

*Primary Examiner* — Long V Le
*Assistant Examiner* — Colin T Sakamoto
(74) *Attorney, Agent, or Firm* — Birch, Stewart, Kolasch & Birch, LLP (57) ABSTRACT

An ultrasound diagnostic apparatus includes an operating unit which sets multistage focus positions through operation by an operator, and a multistage focus position correction unit which, when an inter-focus position distance at the multistage focus positions set through the operating unit exceeds an allowable range set in advance for each measurement depth, automatically corrects the multistage focus positions so as to be within the allowable range.

14 Claims, 4 Drawing Sheets

ULTRASOUND DIAGNOSTIC APPARATUS AND METHOD OF PRODUCING ULTRASOUND IMAGE

BACKGROUND OF THE INVENTION

The present invention relates to an ultrasound diagnostic apparatus and a method of producing an ultrasound image, and in particular, to an ultrasound diagnostic apparatus which produces an ultrasound image on the basis of reception data obtained by processing reception signals output from a transducer array having received an ultrasonic echo from a subject in a reception signal processor.

An ultrasound diagnostic apparatus using an ultrasound image has hitherto been put into practical use in the field of medicine. In general, in this type of ultrasound diagnostic apparatus, an ultrasonic beam is transmitted from a transducer array of an ultrasound probe toward a subject, an ultrasonic echo from the subject is received by the transducer array, and the reception signals are electrically processed in an apparatus body to produce an ultrasound image.

The ultrasonic beam is transmitted from a transducer array with a transmission focus position being defined on each scanning line. While in the vicinity of the transmission focus position, an image with high resolution is obtained because the ultrasonic beam is converged, at a position away from the transmission focus position, the ultrasonic beam is not sufficiently converged, and accordingly, the resolution tends to be lowered.

In view of the above, for example, as in an ultrasound diagnostic apparatus disclosed in JP 2009-22656 A, a technique in which a plurality of transmission focus positions are set in the measurement depth direction of each scanning line by an operator to perform multistage focus transmission is known.

If such a multistage focus transmission is used, the focus of the ultrasonic beam can be narrowed down over a wide range from a region where the measurement depth is small to a region where the measurement depth is large, making it possible to produce a high-quality ultrasound image.

However, if the multistage focus positions on each scanning line set by the operator are excessively close to each other, sound pressure in the vicinity of the focus position increases extremely, and significant irregularity occurs in amplitude of the reception signal, making it difficult to improve image quality over the entire image. The effect produced by closeness of a plurality of focus positions is especially great in a region where the measurement depth is small with little attenuation of ultrasonic waves.

On the contrary, in a region where the measurement depth is large, since attenuation of ultrasonic waves is large, even if the inter-focus position distance at the multistage focus positions is short, irregularity which occurs in the amplitude of the reception signal decreases.

SUMMARY OF THE INVENTION

The invention has been accomplished in order to solve the drawbacks in the prior art, and an object of the invention is to provide an ultrasound diagnostic apparatus and a method of producing an ultrasound image capable of achieving production of a high-quality ultrasound image regardless of an inter-focus position distance at multistage focus positions set by an operator.

An ultrasound diagnostic apparatus according to the present invention comprises:
a transducer array;
a transmission/reception circuit which performs transmission and reception of an ultrasonic beam from the transducer array toward a subject to obtain reception data;
an image producer which produces an ultrasound image on the basis of reception data obtained by the transmission/reception circuit;
a display unit which displays the ultrasound image produced by the image producer;
a controller which performs controls such that the transmission/reception circuit performs transmission and reception of the ultrasonic beam on the basis of multistage focus positions;
an operating unit which sets the multistage focus positions through operation by an operator; and
a multistage focus position correction unit which, when an inter-focus position distance at the multistage focus positions set through the operating unit exceeds an allowable range set in advance for each measurement depth, automatically corrects the multistage focus positions so as to be within the allowable range.

A method of producing an ultrasound image according to the present invention comprises the steps of:
setting multistage focus positions through operation of an operator;
automatically correcting the multistage focus positions so as to be within the allowable range when an inter-focus position distance at the set multistage focus positions exceeds an allowable range set in advance for each measurement depth;
performing transmission and reception of an ultrasonic beam from a transducer array toward a subject on the basis of the corrected multistage focus positions to acquire reception data; and
producing and displaying an ultrasound image on the basis of the acquired reception data.

DETAILED DESCRIPTION OF THE INVENTION

Figure 1:
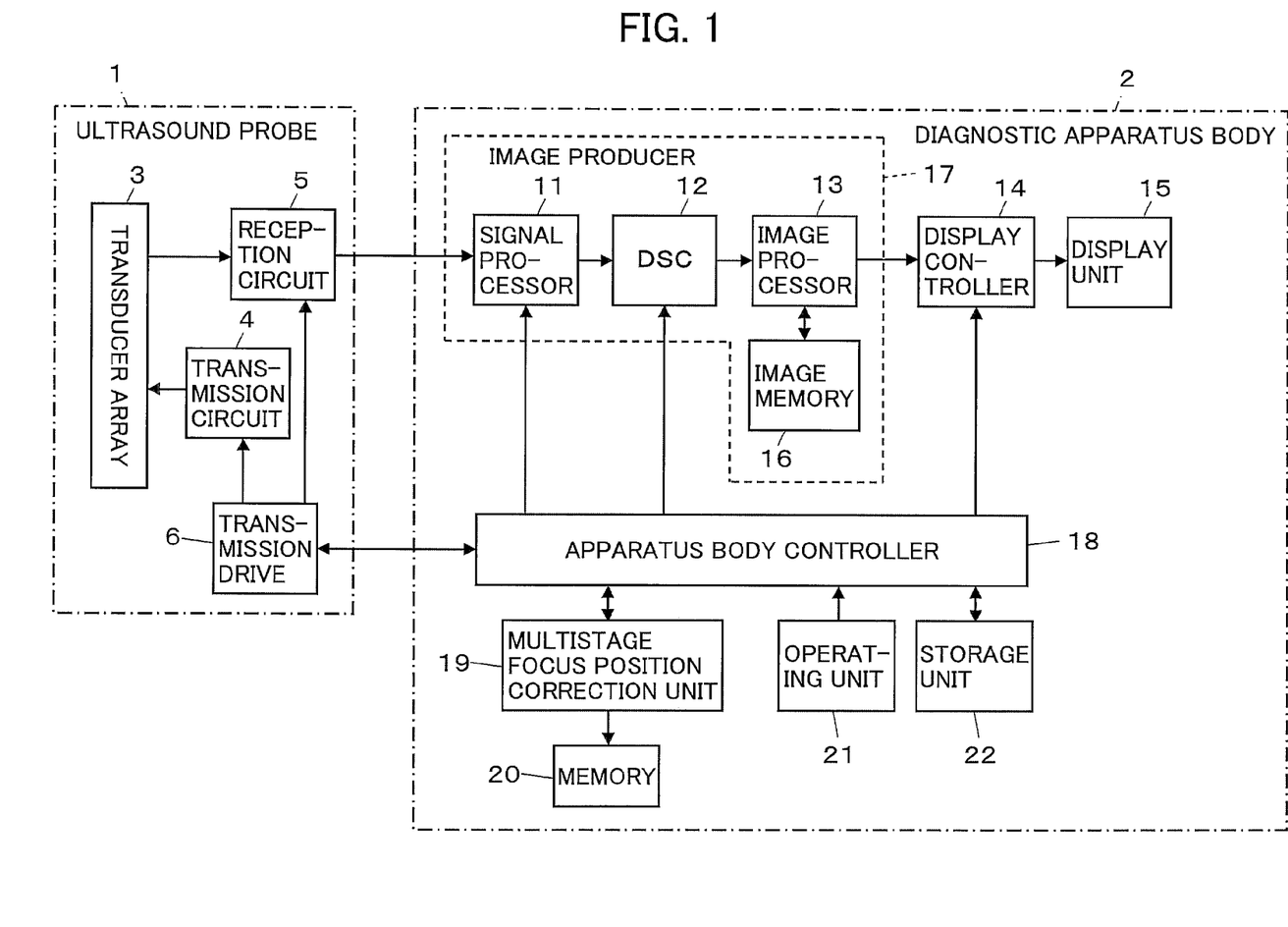
FIG. 1 is a block diagram illustrating a configuration of an ultrasound diagnostic apparatus according to Embodiment 1 of the invention.

Hereinafter, embodiments of the invention will be described with reference to the accompanying drawings.
Embodiment 1
FIG. 1 illustrates a configuration of an ultrasound diagnostic apparatus according to Embodiment 1. The ultrasound diagnostic apparatus includes an ultrasound probe 1, and a diagnostic apparatus body 2 connected to the ultrasound probe 1.

The ultrasound probe 1 has a transducer array 3. A transmission circuit 4 and a reception circuit 5 are connected to the transducer array 3, and a probe controller 6 is connected to the transmission circuit 4 and the reception circuit 5.

The diagnostic apparatus body 2 has a signal processor 11 connected to the reception circuit 5 of the ultrasound probe 1, and a DSC (Digital Scan Converter) 12, an image processor 13, a display controller 14, and a display unit 15 are sequentially connected to the signal processor 11 in this order. An image memory 16 is connected to the image processor 13, and the signal processor 11, the DSC 12, the image processor 13, and the image memory 16 form an image producer 17. An apparatus body controller 18 is connected to the signal processor 11, the DSC 12, and the display controller 14. A multistage focus position correction unit 19 is connected to the apparatus body controller 18, and a memory 20 is connected to the multistage focus position correction unit 19. An operating unit 21 and a storage unit 22 are also connected to the apparatus body controller 18.

The probe controller 6 of the ultrasound probe 1 and the apparatus body controller 18 of the diagnostic apparatus body 2 are connected with each other.

The transducer array 3 of the ultrasound probe 1 has a plurality of ultrasound transducers arranged in a one-dimensional or two-dimensional array. Each of the ultrasound transducers transmits an ultrasonic wave in accordance with an actuation signal supplied from the transmission circuit 4, receives an ultrasonic echo from the subject, and outputs a reception signal. Each ultrasound transducer is constituted by a vibrator in which electrodes are formed at both ends of a piezoelectric body composed of piezoelectric ceramic represented by PZT (lead zirconate titanate), a polymer piezoelectric device such as PVDF (polyvinylidene fluoride), piezoelectric single crystal represented by PMN-PT (lead magnesium niobate-lead titanate solid solution), or the like.

If a pulsed or continuous-wave voltage is applied across the electrodes of the vibrator, the piezoelectric body expands and contracts, whereby pulsed or continuous-wave ultrasonic waves are produced from the vibrators and the produced ultrasonic waves are synthesized to form an ultrasonic beam. When receiving propagating ultrasonic waves, the vibrators expand and contract to produce electric signals, and the electric signals are output as the reception signals of the ultrasonic waves.

The transmission circuit 4 includes, for example, a plurality of pulse generators. The transmission circuit 4 adjusts the delay amount of each of the actuation signals on the basis of a transmission delay pattern selected in response to a control signal from the probe controller 6 such that ultrasonic waves transmitted from the plurality of ultrasound transducers of the transducer array 3 form an ultrasonic beam, and supplies the adjusted actuation signals to the ultrasound transducers.

The reception circuit 5 amplifies the reception signals output from the ultrasound transducers of the transducer array 3, and performs A/D conversion for the amplified reception signals. The reception circuit 5, thereafter, performs a reception focus process by giving a delay to each of the reception signals in accordance with sound speed or the distribution of sound speed set on the basis of a reception delay pattern selected in response to a control signal from the probe controller 6, and adding the reception signals. With this reception focus process, the focus of the ultrasonic echo is narrowed down to produce reception data (sound ray signal).

The probe controller 6 controls the respective units of the ultrasound probe 1 on the basis of various control signals transmitted from the apparatus body controller 18 of the diagnostic apparatus body 2.

The signal processor 11 of the diagnostic apparatus body 2 performs correction of attenuation depending on distance in accordance with the depth of the reflection position of the ultrasonic wave on reception data produced by the reception circuit 5 of the ultrasound probe 1, and then performs an envelope detection process to produce a B-mode image signal which is tomographic image information relating to the tissue of the subject.

The DSC 12 converts (raster-converts) the B-mode image signal produced by the signal processor 11 to an image signal based on a normal television signal scanning system.

The image processor 13 performs various necessary image processing, such as a gradation processing, on the B-mode image signal input from the DSC 12, and outputs the processed B-mode image signal to the display controller 14 or stores the processed B-mode image signal in the image memory 16.

The display controller 14 causes the display unit 15 to display an ultrasound diagnostic image on the basis of the B-mode image signal subjected to the image processing by the image processor 13.

The display unit 15 includes, for example, a display device, such as an LCD, and displays the ultrasound diagnostic image under the control of the display controller 14.

The operating unit 21 is used when the operator performs an input operation, and may be constituted by a keyboard, a mouse, a trackball, a touch panel, or the like. At the time of multistage focus transmission, the multistage focus positions on each scanning line are set by the operator through the operating unit 21.

The storage unit 22 stores an operation program or the like, and a recording medium such as hard disk, flexible disk, MO, MT, RAM, CD-ROM, DVD-ROM, SD card, CF card and USB memory, or a server may be used as the storage unit 22.

The multistage focus position correction unit 19 compares the inter-focus position distance of the multistage focus positions on each scanning line input and set by the operator through the operating unit 21 at the time of multistage focus transmission with an allowable range set in advance for each measurement depth, and when the inter-focus position distance exceeds the allowable range, automatically corrects the multistage focus positions such that the inter-focus position distance is within the allowable range.

The memory 20 contains an inter-focus position distance table, in which the allowable range of the inter-focus position distance is correlated with the measurement depth. The allowable range of the inter-focus position distance indicates the inter-focus position distance for each measurement depth such that, when multistage focus transmission is performed, degradation of image quality of an ultrasound image due to an extreme increase in sound pressure in the vicinity of a focus position is not caused.

The multistage focus position correction unit 19 corrects the multistage focus positions with reference to the inter-focus position distance table stored in the memory 20.

The apparatus body controller 18 controls the respective units in the diagnostic apparatus body 2 on the basis of various command signals and the like input from the operating unit 21 by the operator.

Although in Embodiment 1, the signal processor 11, the DSC 12, the image processor 13, the display controller 14, and the multistage focus position correction unit 19 are constituted by a CPU and an operation program which causes the CPU to perform various processing, these may be constituted by digital circuits.

Next, the operation of Embodiment 1 will be described.

First, prior to ultrasound diagnosis using multistage focus transmission, multistage focus positions on each scanning line are set by the operator through the operating unit 21. It is assumed that two focus points are set on each scanning line.

Figure 2:
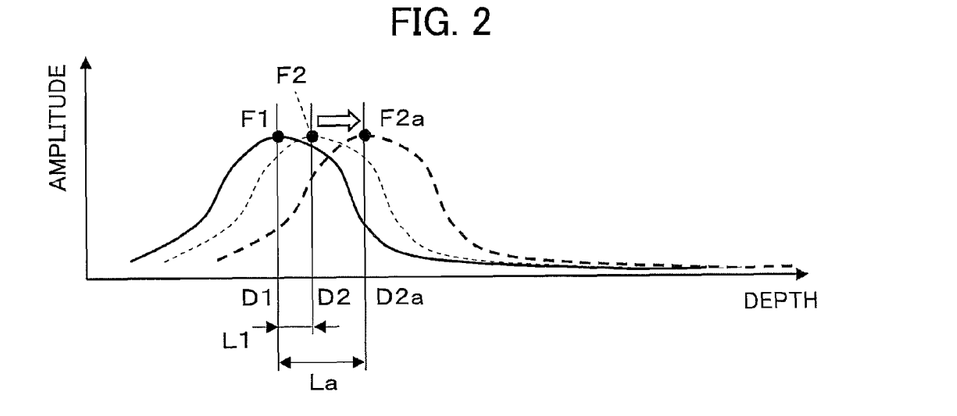
FIG. 2 is a diagram showing an operation of Embodiment 1.

For example, as shown in FIG. 2, if on a certain scanning line, a first focus point F1 is set at a depth D1, and then a second focus point F2 is set at a depth D2 larger than the depth D1, the depth D1 of the first focus point F1 and the depth D2 of the second focus point F2 are input from the operating unit 21 to the multistage focus position correction unit 19 through the apparatus body controller 18.

If the depth D1 of the first focus point F1 and the depth D2 of the second focus point F2 are input through the apparatus body controller 18, the multistage focus position correction unit 19 calculates the inter-focus position distance L1 between the first focus point F1 and the second focus point F2 from the depths D1 and D2, and compares the inter-focus position distance L1 with the allowable range of the inter-focus position distance table stored in advance in the memory 20. In the inter-focus position distance table, the allowable range of the inter-focus position distance for each measurement depth is defined, and if it is assumed that an allowable lower limit value La is correlated with the depth D1 of the first focus point F1, the multistage focus position correction unit 19 compares the inter-focus position distance L1 between the first focus point F1 and the second focus point F2 with the allowable lower limit value La correlated with the depth D1 of the first focus point F1.

As shown in FIG. 2, when the inter-focus position distance L1 is smaller than the allowable lower limit value La, the position of the second focus point F2 is automatically corrected by the multistage focus position correction unit 19 until the inter-focus position distance between the first focus point F1 and the second focus point F2 becomes the allowable lower limit value La. That is, a new second focus point F2a is set at a depth D2a which is larger than the depth D1 of the first focus point F1 by the allowable lower limit value La.

In this way, on the basis of the first focus point F1 set by the operator and the second focus point F2a newly set by the multistage focus position correction unit 19, ultrasonic beams are sequentially transmitted from the ultrasound transducers of the transducer array 3 in accordance with the actuation signals from the transmission circuit 4 of the ultrasound probe 1. Reception signals received by the ultrasound transducers are sequentially output to the reception circuit 5, such that reception data is produced.

Similarly, two focus points are set on other scanning lines, and transmission and reception of ultrasonic beams are sequentially performed, such that reception data is produced.

An image signal is produced by the image producer 17 of the diagnostic apparatus body 2 on the basis of reception data, and an ultrasound image is displayed on the display unit 15 by the display controller 14.

At this time, the position of the second focus point F2 is automatically corrected by the multistage focus position correction unit 19 such that the inter-focus position distance between the first focus point F1 and the second focus point F2 becomes the allowable lower limit value La. For this reason, even if the first focus point F1 and the second focus point F2 are set by the operator such that the inter-focus position distance therebetween is less than the allowable lower limit value La, it is possible to prevent the occurrence of great irregularity in the level of the reception signal due to an extreme increase in sound pressure in the vicinity of a focus position, making it possible to produce a high-quality ultrasound image.

When the inter-focus position distance between the first focus point F1 and the second focus point F2 set by the operator is already equal to or larger than the allowable lower limit value La, any correction by the multistage focus position correction unit 19 is not performed, transmission and reception of an ultrasonic beam is performed on the basis of the first focus point F1 and the second focus point F2, and an ultrasound image is produced.

In a region where the measurement depth is large, since attenuation of ultrasonic waves is comparatively large, even if the inter-focus position distance of a plurality of focus points is short, there is no case where sound pressure in the vicinity of a focus position increases extremely. For this reason, Embodiment 1 is particularly useful in a region whose measurement depth is smaller than a predetermined measurement depth.

In Embodiment 1 described above, when the operator sets the second focus point F2 at the depth D2 larger than the depth D1 of the first focus point F1, the depth D1 of the first focus point F1 is used as a reference, the allowable lower limit value La correlated with the depth D1 and the inter-focus position distance L1 are compared with each other, and when the inter-focus position distance L1 is smaller than the allowable lower limit value La, the first focus point F1 on the shallow side is fixed to correct the second focus point F2 on the deep side. However, the invention is not limited thereto.

Figure 3:
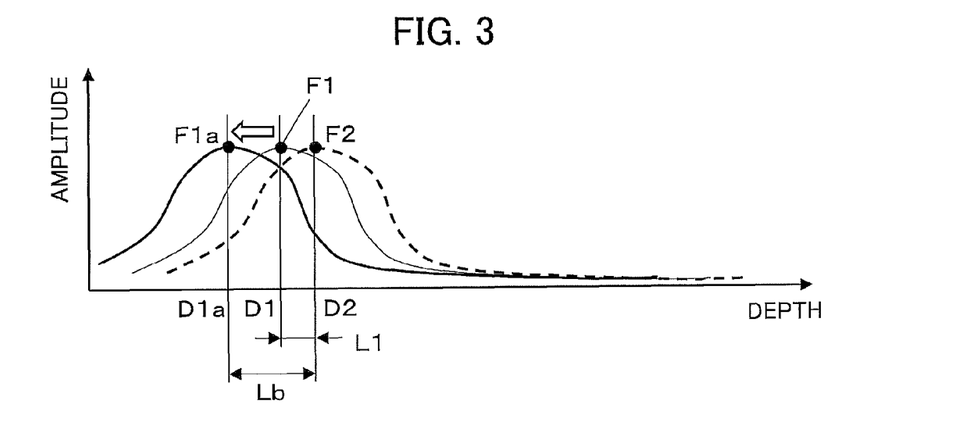
FIG. 3 is a diagram showing an operation of a modification of Embodiment 1.

For example, a focus position being set through the operating unit 21 may be fixed to correct a focus position which has already been set. That is, as shown in FIG. 3, if the operator sets the first focus point F1 at the depth D1 and then sets the second focus point F2 at the depth D2 larger than the depth D1, the multistage focus position correction unit 19 reads the allowable range correlated with the depth D2 of the second focus point F2 from the inter-focus position distance table in the memory 20, and compares the inter-focus position distance L1 with the allowable range.

If it is assumed that an allowable lower limit value Lb as the allowable range is correlated with the depth D2 of the second focus point F2, the inter-focus position distance L1 is compared with the allowable lower limit value Lb, and when the inter-focus position distance L1 is smaller than the allowable lower limit value Lb, the multistage focus position correction unit 19 automatically corrects the position of the first focus point F1 on the shallow side which has already been set until the inter-focus position distance between the first focus point F1 and the second focus point F2 becomes the allowable lower limit value Lb. Thus, the first focus point F1 is further moved to the shallow side, and a new first focus point F1a is set at a depth D1a which is smaller than the depth D2 of the second focus point F2 by the allowable lower limit value Lb.

In this way, similarly, it also becomes possible to produce a high-quality ultrasound image.

Embodiment 2

In a region where the measurement depth is large, since attenuation of ultrasonic waves is comparatively large, even if the inter-focus position distance between a plurality of focus points is short, there is no concern that sound pressure in the vicinity of a focus position increases extremely, and in addition, the amounts of attenuation of ultrasonic waves at respective focus points are compensated for with each other. Thus, it is possible to acquire more satisfactory reception signals.

Accordingly, in Embodiment 2, in the inter-focus position distance table stored in the memory 20, an allowable upper limit value as the allowable range is correlated with each measurement depth in a region whose measurement depth is equal to or larger than a predetermined measurement depth.

That is, in a region whose measurement depth is equal to or larger than the predetermined measurement depth, the inter-focus position distance between the focus points is corrected so as not to exceed the allowable upper limit value defined in the inter-focus position distance table.

Figure 4:
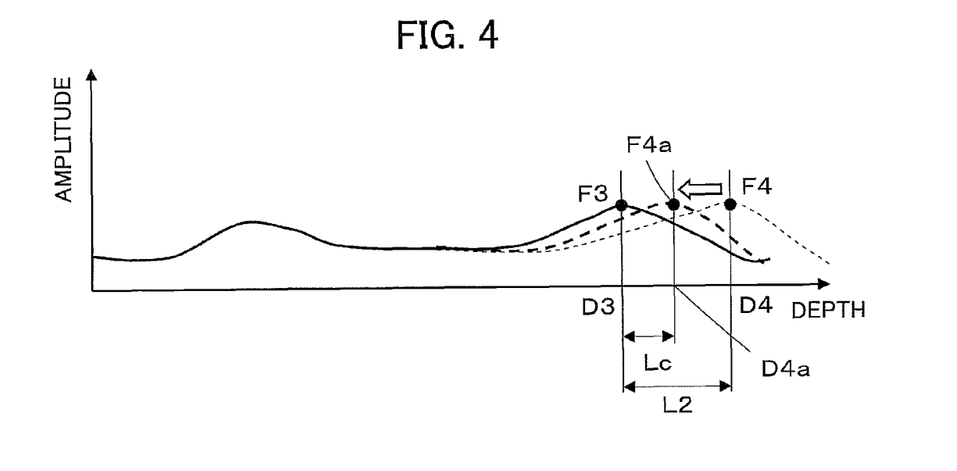
FIG. 4 is a diagram showing an operation of Embodiment 2.

For example, as shown in FIG. 4, if the operator sets a first focus point F3 at a depth D3 in a region where measurement depth is equal to or larger than a predetermined measurement depth and then sets a second focus point F4 at a depth D4 larger than the depth D3, the multistage focus position correction unit 19 calculates the inter-focus position distance L2 between the first focus point F3 and the second focus point F4, and reads the allowable range correlated with the depth D3 of the first focus point F3 from the inter-focus position distance table in the memory 20.

If it is assumed that an allowable upper limit value Lc as the allowable range is correlated with the depth D3 of the first focus point F3, the multistage focus position correction unit 19 compares the inter-focus position distance L2 with the allowable upper limit value Lc.

As shown in FIG. 4, when the inter-focus position distance L2 exceeds the allowable upper limit value Lc, the multistage focus position correction unit 19 automatically corrects the position of the second focus point F4 until the inter-focus position distance between the first focus point F3 and the second focus point F4 becomes the allowable upper limit value Lc. That is, the second focus point F4 is moved to the shallow side, and a new second focus point F4a is set at a depth D4a which is larger than the depth D3 of the first focus point F3 by the allowable upper limit value Lc.

Transmission and reception of an ultrasonic beam are performed on the basis of the first focus point F3 and the second focus point F4a set in the above-described manner, and an ultrasound image is produced.

Thus, the amount of attenuation of ultrasonic waves is compensated for in a region whose measurement depth is equal to or larger than a predetermined measurement depth, making it possible to produce a high-quality ultrasound image also in the above-mentioned region whose measurement depth is equal to or larger than the predetermined measurement depth.

Also in Embodiment 2, from among the first focus point F3 and the second focus point F4 set by the operator, a focus position being set through the operating unit 21 may be fixed to correct a focus position which has already been set.

Embodiment 3

Although in Embodiments 1 and 2 described above, two focus points are set on each scanning line, the invention is not limited thereto, and three or more focus points may be set on each scanning line.

Figure 5:
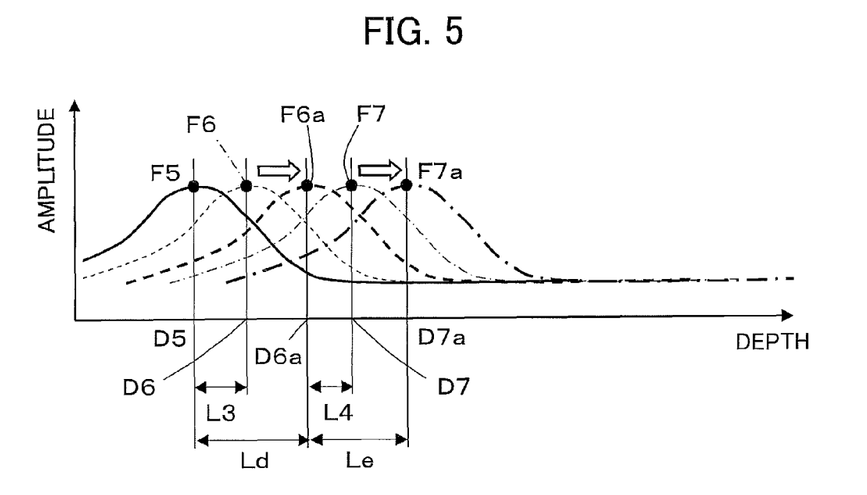
FIG. 5 is a diagram showing an operation of Embodiment 3.

For example, as shown in FIG. 5, if the operator sets a first focus point F5 at a depth D5 and then sets a second focus point F6 at a depth D6 larger than the depth D5, the multistage focus position correction unit 19 calculates the inter-focus position distance L3 between the first focus point F5 and the second focus point F6, and reads the allowable range correlated with the depth D5 of the first focus point F5 from the inter-focus position distance table in the memory 20.

If it is assumed that an allowable lower limit value Ld as the allowable range is correlated with the depth D5 of the first focus point F5, the multistage focus position correction unit 19 compares the inter-focus position distance L3 with the allowable lower limit value Ld.

As shown in FIG. 5, when the inter-focus position distance L3 is smaller than the allowable lower limit value Ld, the multistage focus position correction unit 19 automatically corrects the position of the second focus point F6 until the inter-focus position distance between the first focus point F5 and the second focus point F6 becomes the allowable lower limit value Ld. That is, the second focus point F6 is moved to the deep side, and a new second focus point F6a is set as a depth D6a which is larger than the depth D5 of the first focus point F5 by the allowable lower limit value Ld.

When the operator sets a third focus point F7 at a depth D7 larger than the depth D6a of the new second focus point F6a, the multistage focus position correction unit 19 calculates the inter-focus position distance L4 between the new second focus point F6a and the third focus point F7, and reads the allowable range correlated with the depth D6a of the new second focus point F6a from the inter-focus position distance table in the memory 20.

If it is assumed that an allowable lower limit value Le as the allowable range is correlated with the depth D6a of the new second focus point F6a, the multistage focus position correction unit 19 compares the inter-focus position distance L4 with the allowable lower limit value Le.

As shown in FIG. 5, when the inter-focus position distance L4 is smaller than the allowable lower limit value Le, the multistage focus position correction unit 19 automatically corrects the position of the third focus point F7 until the inter-focus position distance between the new second focus point F6a and the third focus point F7 becomes the allowable lower limit value Le. That is, the third focus point F7 is moved to the deep side, and a new third focus point F7a is set at a depth D7a which is larger than the depth D6a of the new second focus point F6a by the allowable lower limit value Le.

Transmission and reception of an ultrasonic beam are performed on the basis of the first focus point F5, the new second focus point F6a and the new third focus point F7a set in the above-described manner, and an ultrasound image is produced.

In FIG. 5, the operator sequentially sets the three focus points F5 to F7 through the operating unit 21 in the order of increasing depth with fixing the focus point that has been already set, correcting the next focus point being newly set as necessary. Conversely, a focus position being set through the operating unit 21 may be fixed instead and a focus position which has already been set may be corrected. Meanwhile, when the setting of the two focus points has already been completed, if the third focus point which is newly set is fixed, it is necessary to correct both two focus points, which have already been set. Accordingly, it is desirable that the third focus point which is newly set is corrected.

Although when the operator sets the three focus points F5 to F7 through the operating unit 21, the multistage focus position correction unit 19 corrects the focus positions one by one with reference to the inter-focus position distance table in which the allowable range of the inter-focus position distance is correlated with each measurement depth, the invention is not limited thereto, and an inter-focus position distance table in which both of an allowable range of an inter-focus position distance on a shallow side and an allowable range of an inter-focus position distance on a deep side are correlated with each measurement depth may be used. After the operator sets the three focus points F5 to F7, the multistage focus position correction unit 19 fixes the focus point F6 in the middle portion from among the three focus points F5 to F7 with reference to the inter-focus position distance table and also corrects the remaining two focus points F5 and F7.

Figure 6:
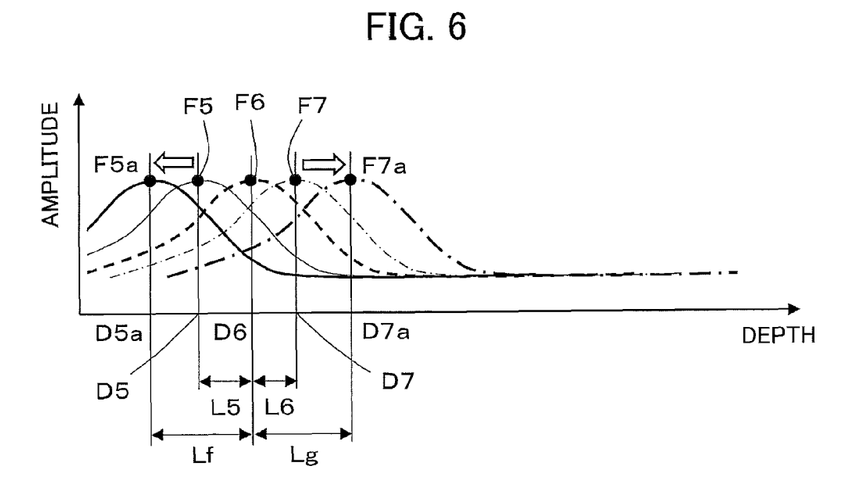
FIG. 6 is a diagram showing an operation of a modification of Embodiment 3.

For example, as shown in FIG. 6, it is assumed that the operator sets the first focus point F5 at the depth D5, the second focus point F6 at the depth D6, and the third focus point F7 at the depth D7 sequentially from the shallow side to the deep side through the operating unit 21. After the three focus points F5 to F7 are set in the above-described manner, the multistage focus position correction unit 19 calculates the inter-focus position distance L5 between the first focus point F5 and the second focus point F6 and the inter-focus position distance L6 between the second focus point F6 and the third focus point F7, and reads the allowable range on the shallow side and the allowable range on the deep side which are correlated with the depth D6 of the second focus point F6 existing in the middle portion from among the three focus points F5 to F7 from the inter-focus distance table in the memory 20.

If it is assumed that an allowable lower limit value Lf as the allowable range on the shallow side and an allowable lower limit value Lg as the allowable range on the deep side are correlated with the depth D6 of the second focus point F6, the multistage focus position correction unit 19 compares the inter-focus position distance L5 with the allowable lower limit value Lf and also compares the inter-focus position distance L6 with the allowable lower limit value Lg.

As shown in FIG. 6, when the inter-focus position distance L5 between the first focus point F5 and the second focus point F6 is smaller than the allowable lower limit value Lf, the multistage focus position correction unit 19 automatically corrects the position of the first focus point F5 until the inter-focus position distance between the first focus point F5 and the second focus point F6 becomes the allowable lower limit value Lf. That is, the first focus point F5 is moved to the shallow side, and a new first focus point F5a is set at a depth D5a which is smaller than the depth D6 of the second focus point F6 by the allowable lower limit value Lf.

Similarly, when the inter-focus position distance L6 between the second focus point F6 and the third focus point F7 is smaller than the allowable lower limit value Lg, the multistage focus position correction unit 19 automatically corrects the position of the third focus point F7 until the inter-focus position distance between the second focus point F6 and the third focus point F7 becomes the allowable lower limit value Lg. That is, the third focus point F7 is moved to the deep side, and a new third focus point F7a is set at a depth D7a which is larger than the depth D6 of the second focus point F6 by the allowable lower limit value Lg.

As in Embodiment 2, an allowable upper limit value as an allowable range of an inter-focus position distance may be correlated with a measurement depth in a region whose measurement depth is equal to or larger than a predetermined measurement depth. Therefore, even if three focus points are set on each scanning line, the amount of attenuation of ultrasonic waves in the deep region is compensated for, making it possible to produce a high-quality ultrasound image.

Although in Embodiment 3, a case where the three focus points are set on each scanning line has been illustrated, similarly, four or more focus points may be set on each scanning line.

Embodiment 4

Since in Embodiments 1 to 3 described above, the multistage focus position correction unit 19 automatically corrects the multistage focus positions, it is desirable to make the operator recognize the corrected focus point.

Accordingly, in Embodiment 4, the focus position corrected by the multistage focus position correction unit 19 is displayed.

Figure 7:
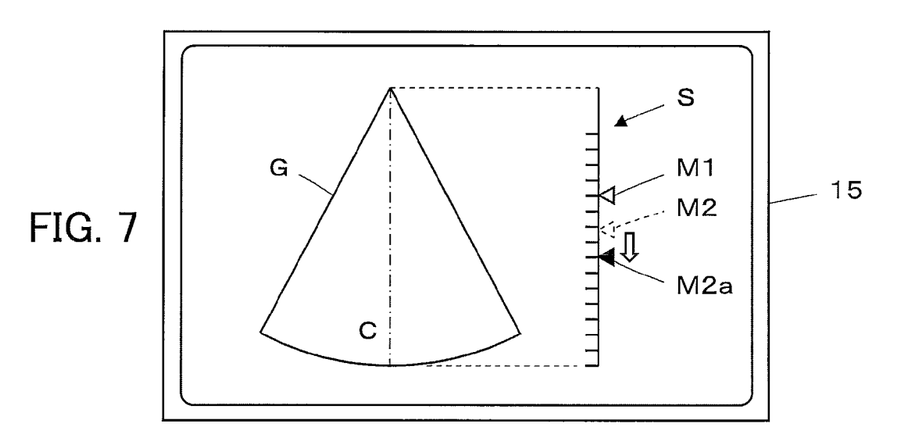
FIG. 7 is a diagram showing a display screen in Embodiment 4.

As shown in FIG. 7, in the display unit 15 on which an ultrasound image G is displayed, a scale S of a measurement depth is displayed corresponding to the ultrasound image G, and positions of a plurality of focus points are displayed. At this time, for example, the positions of focus points on a central scanning line C in a scanning direction may be representatively displayed on the scale S.

In FIG. 7, if the operator sets a first focus point through the operating unit 21, the position of the first focus point in the depth direction is indicated by a mark M1, and if the operator subsequently sets a second focus point, the position of the second focus point in the depth direction is indicated by a mark M2. Meanwhile, since the inter-focus position distance between the first focus point and the second focus point is smaller than the allowable lower limit value, the second focus point is automatically corrected by the multistage focus position correction unit 19, and a new second focus point is set. The position of the new second focus point is indicated by a mark M2a.

At this time, in order to distinguish the mark M2 corresponding to the second focus point which is input by the operator but is actually unused and will be corrected by the multistage focus position correction unit 19 from the mark M1 corresponding to the first focus point and the mark M2a corresponding to the new second focus point which are actually set and used for multistage focus transmission, it is desirable to display at least the mark M2 with a color, a shape, or the like different from the other marks M1 and M2a.

In FIG. 7, the mark M2 which is actually unused is displayed in a broken-line triangular shape and the marks M1 and M2a which are actually used are displayed in a solid-line triangular shape. The mark M1 corresponding to the first focus point which is input by the operator and set directly as a focus point is displayed in a white triangular shape, and the mark M2a corresponding to the new second focus point which is automatically produced by the multistage focus position correction unit 19 is displayed in a black triangular shape.

Furthermore, since the mark M2 which is displayed in a broken-line triangular shape is input by the operator but is actually unused, it is desirable that the display is automatically erased, for example, when a predetermined time elapses after the new mark M2a is displayed by the multistage focus position correction unit 19, or the display is erased manually. This is to prevent the marks from increasing in number and thus to keep ease of recognition in display.

Figure 8:
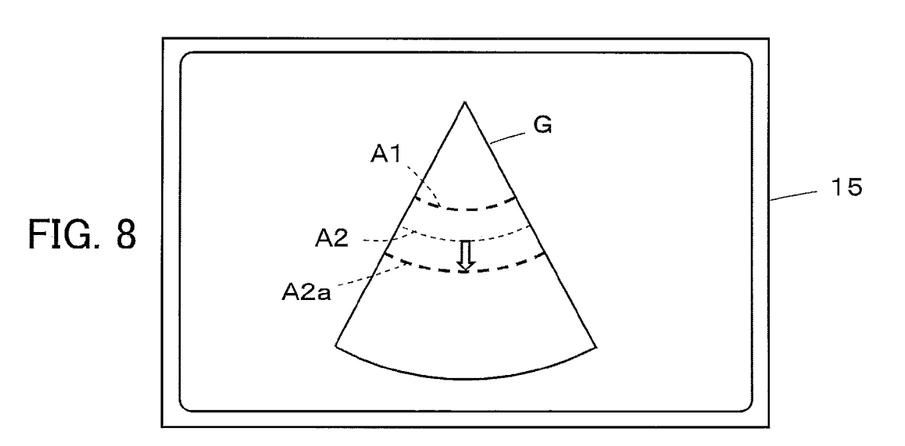
FIG. 8 is a diagram showing a display screen in a modification of Embodiment 4.

Instead of displaying the scale S, as shown in FIG. 8, a focus line may be displayed on the ultrasound image G in an overlapping manner. First focus points on a plurality of scanning lines set by the operator are connected together, such that a first focus line A1 is displayed on the ultrasound image G in an overlapping manner, and second focus points on the plurality of scanning lines set by the operator are connected together, such that a second focus line A2 is displayed on the ultrasound image G in an overlapping manner. Further, new second focus points which are produced when the multistage focus position correction unit 19 automatically corrects the second focus points on the scanning lines are connected together, such that a new second focus line A2a is displayed on the ultrasound image G in an overlapping manner.

Also in this case, in order to distinguish the second focus line A2 which is actually unused from the other focus lines A1 and A2a, it is desirable to display at least the second focus line A2 with a color, a line, or the like different from the other focus lines A1 and A2a.

In FIG. 8, the focus lines A1 and A2a which are actually used are displayed with a broken line, and the second focus line A2 which is actually unused is displayed with a broken line thinner than the other focus lines A1 and A2a.

Since the focus lines A1, A2, and A2a are displayed on the ultrasound image G in an overlapping manner, if the display continues as it is, this may affect diagnosis. Accordingly, it is desirable that the display of these focus lines is automatically erased when a predetermined time elapses from the display, or the display is erased manually.

In this way, if the focus lines are displayed on the ultrasound image G in an overlapping manner, it is possible to recognize the multistage focus positions more sensitively, making it possible to perform ultrasound diagnosis efficiently.

Figure 9:
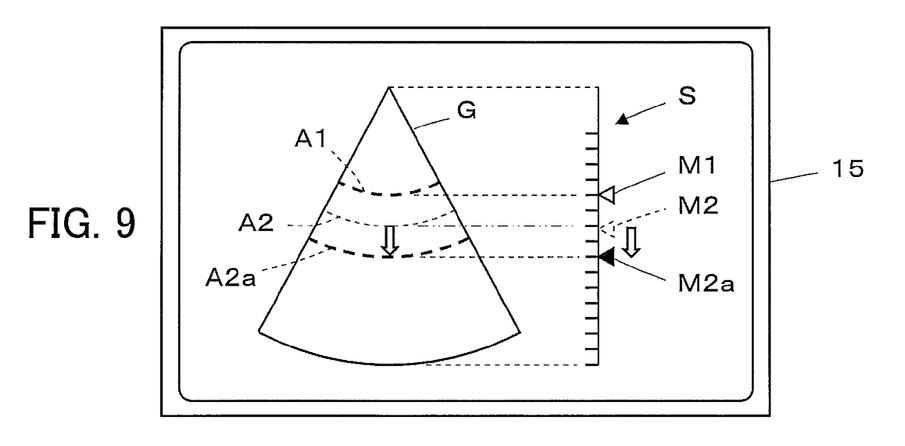
FIG. 9 is a diagram showing a display screen in another modification of Embodiment 4.

As shown in FIG. 9, the positions of a plurality of focus points may be displayed on the scale S of the measurement depth with the marks M1, M2, and M2a, and simultaneously, a plurality of focus lines A1, A2, and A2a may be displayed on the ultrasound image G in an overlapping manner.

The connection of the ultrasound probe 1 and the diagnostic apparatus body 2 in Embodiments 1 to 4 described above may be either wired connection or connection by wireless communication.

What is claimed is:

1. An ultrasound diagnostic apparatus comprising:
    a transducer array;
    a transmission/reception circuit configured to perform transmission and reception of an ultrasonic beam from the transducer array toward a measurement region of a subject to obtain reception data;
    an image producer circuit configured to produce an ultrasound image on the basis of reception data obtained by the transmission/reception circuit;
    a display device configured to display the ultrasound image produced by the image producer circuit;
    an operating device configured to set multistage focus positions selected from a plurality of measurement depths within the measurement region through operation by an operator;
    a memory which in advance stores an inter-focus position distance table in which an allowable range of an inter-focus position distance for each measurement depth of the plurality of measurement depths is defined, wherein the allowable range for each measurement depth indicates the inter-focus position distance at which degradation of image quality of the ultrasound image due to an extreme increase in sound pressure in the vicinity of a focus position is not caused;
    a multistage focus position correction processor configured to read the allowable range for the measurement depth corresponding to the selected measurement depths of the multistage focus positions set through the operating device from the inter-focus position distance table in the memory, verify an inter-focus position distance between the selected measurement depths of the multistage focus positions set through the operating device is within the read allowable range, and automatically correct the multistage focus positions so as to be within the allowable range if the inter-focus position distance exceeds the allowable range; and
    a control circuit configured to control the transmission/reception circuit to perform transmission and reception of the ultrasonic beam on the basis of multistage focus positioning using the multistage focus positions verified or corrected by the multistage focus position correction processor.

2. The ultrasound diagnostic apparatus according to claim 1,
    wherein the multistage focus position correction processor is configured to correct the multistage focus positions on the basis of an allowable lower limit value set in advance for each measurement depth of a plurality of measurement depths smaller than a predetermined measurement depth and within the measurement region.

3. The ultrasound diagnostic apparatus according to claim 1,
    wherein the multistage focus position correction processor is configured to correct the multistage focus positions on the basis of an allowable upper limit value set in advance for each measurement depth of the plurality of measurement depths equal to or larger than a predetermined depth and within the measurement region.

4. The ultrasound diagnostic apparatus according to claim 1,
    wherein the multistage focus position correction processor is configured to correct the multistage focus positions on the basis of an allowable lower limit value set in advance for each measurement depth of a plurality of measurement depths smaller than a predetermined measurement depth and within the measurement region, and correct the multistage focus positions on the basis of an allowable upper limit value set in advance for each measurement depth of a plurality of measurement depths equal to or larger than the predetermined measurement depth and within the measurement region.

5. The ultrasound diagnostic apparatus according to claim 4,
    wherein the inter-focus position distance table is a table in which an allowable range of an inter-focus position distance on a shallow side and an allowable range of an inter-focus position distance on a deep side are respectively correlated with each other for each measurement depth.

6. The ultrasound diagnostic apparatus according to claim 1,
    wherein the multistage focus position correction processor is configured to fix a shallowest focus position from among the multistage focus positions to correct a focus position on a deep side.

7. The ultrasound diagnostic apparatus according to claim 4,
    wherein the multistage focus position correction processor is configured to fix a shallowest focus position from among the multistage focus positions to correct a focus position on a deep side.

8. The ultrasound diagnostic apparatus according to claim 1,
    wherein, the multistage focus position correction processor is configured to fix a focus position being set through the operating device from among the multistage focus positions to correct other focus positions.

9. The ultrasound diagnostic apparatus according to claim 4,
    wherein the multistage focus position correction processor is configured to fix a focus position being set through the operating device from among the multistage focus positions to correct other focus positions.

10. The ultrasound diagnostic apparatus according to claim 1,
    wherein the display device is configured to display the multistage focus positions corrected by the multistage focus position correction processor.

11. The ultrasound diagnostic apparatus according to claim 4,
    wherein the display device is configured to display the multistage focus positions corrected by the multistage focus position correction processor.

12. The ultrasound diagnostic apparatus according to claim 7, wherein the display device is configured to display the multistage focus positions corrected by the multistage focus position correction processor.

13. The ultrasound diagnostic apparatus according to claim 9,
wherein the display device is configured to display the multistage focus positions corrected by the multistage focus position correction processor.

14. A method of producing an ultrasound image, the method comprising the steps of:

storing, in advance in a memory, an inter-focus position distance table in which an allowable range of an inter-focus position distance for each measurement depth of a plurality of measurement depths is defined, wherein the allowable range for each measurement depth indicates the inter-focus position distance at which degradation of image quality of the ultrasound image due to an extreme increase in sound pressure in the vicinity of a focus position is not caused;

setting multistage focus positions within a measurement region of a subject selected from the plurality of measurement depths through operation of an operating device by an operator;

reading the allowable range for the measurement depth corresponding to the selected measurement depths of the set multistage focus positions from the inter-focus position distance table in memory;

verifying an inter-focus position distance between the selected measurement depths of the set multistage focus positions is within the read allowable range;

automatically correcting the multistage focus positions so as to be within the allowable range if the inter-focus position distance exceeds the allowable range;

performing transmission and reception of an ultrasonic beam from a transducer array toward the measurement region of the subject on the basis of the verified or corrected multistage focus positions to acquire reception data; and producing and displaying an ultrasound image on the basis of the acquired reception data on a display device.

* * * * *